United States Patent
Burton et al.

(10) Patent No.: US 9,682,945 B2
(45) Date of Patent: Jun. 20, 2017

(54) EMM-23 MOLECULAR SIEVE MATERIAL, ITS SYNTHESIS AND USE

(71) Applicant: ExxonMobil Chemical Patents Inc., Baytown, TX (US)

(72) Inventors: Allen W. Burton, Stewartsville, NJ (US); Karl G. Strohmaier, Port Murray, NJ (US); Hilda B. Vroman, Piscataway, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/918,968

(22) Filed: Oct. 21, 2015

(65) Prior Publication Data

US 2016/0039779 A1 Feb. 11, 2016

Related U.S. Application Data

(62) Division of application No. 14/235,419, filed on Mar. 12, 2014, now Pat. No. 9,205,416.

(60) Provisional application No. PCT/US2012/047910, filed on Jul. 24, 2012, provisional application No. 61/514,939, filed on Aug. 4, 2011.

(30) Foreign Application Priority Data

Sep. 19, 2011 (EP) .................................... 11181734

(51) Int. Cl.
| | | |
|---|---|---|
| C07D 295/037 | (2006.01) |
| B01J 29/86 | (2006.01) |
| B01J 29/87 | (2006.01) |
| B01J 29/89 | (2006.01) |
| C01B 37/00 | (2006.01) |
| C01B 37/02 | (2006.01) |
| C01B 39/48 | (2006.01) |
| B01J 29/70 | (2006.01) |
| B01J 35/00 | (2006.01) |

(52) U.S. Cl.
CPC .......... *C07D 295/037* (2013.01); *B01J 29/70* (2013.01); *B01J 29/7007* (2013.01); *B01J 29/86* (2013.01); *B01J 29/87* (2013.01); *B01J 29/89* (2013.01); *B01J 35/002* (2013.01); *C01B 37/00* (2013.01); *C01B 37/02* (2013.01); *C01B 39/48* (2013.01)

(58) Field of Classification Search
CPC .................................................. C07D 295/037
See application file for complete search history.

(56) References Cited

U.S. PATENT DOCUMENTS

| | | | |
|---|---|---|---|
| 4,941,963 A | 7/1990 | Valyocsik |
| 6,136,290 A | 10/2000 | Benazzi et al. |

FOREIGN PATENT DOCUMENTS

EP 0 135 658 4/1985

OTHER PUBLICATIONS

Jackowski et al., "*Diquaternary ammonium compounds in zeolite synthesis: cyclic and polycyclic N-heterocycles connected by methylene chains*", Journal of the American Chemical Society, vol. 131, No. 3, Jan. 7, 2009; pp. 1092-1100.

Lee et al., "*Synthesis and Characterization of ERI-Type UZM-12 Zeolites and their Methanol-to-Olefin Performance*", Journal of the American Chemical Society, vol. 132, No. 7, 2010, pp. 12971-12982.

Maple et al., "*Synthesis and characterisation of aluminophosphate-based zeotype materials prepared with a, ω-bis(N-methylpyrrolidinium) alkane cations as structure-directing agents*", Dalton Transactions 2007 the Royal Society of Chemistry, No. 37, 2007, pp. 4175-4181.

*Primary Examiner* — Rebecca Anderson
*Assistant Examiner* — Karen Cheng
(74) *Attorney, Agent, or Firm* — Darryl M. Tyus (57) ABSTRACT

A new molecular sieve material is designated as EMM-23 and has, in its as-calcined form, an X-ray diffraction pattern including the following peaks in Table 1:

TABLE 1

| d-spacing (Å) | Relative Intensity [100 × I/I(o)] |
|---|---|
| 17.5-16.3 | 60-100 |
| 10.6-10.1 | 5-50 |
| 9.99-9.56 | 20-70 |
| 6.23-6.06 | 1-10 |
| 5.84-5.69 | 1-10 |
| 5.54-5.40 | 1-10 |
| 4.29-4.21 | 1-10 |
| 3.932-3.864 | 1-10 |
| 3.766-3.704 | 5-40 |
| 3.735-3.674 | 1-10 |
| 3.657-3.598 | 1-10 |
| 3.595-3.539 | 1-20 |

2 Claims, 4 Drawing Sheets

Figure 1 (a), upper; Figure 1 (b), lower

EMM-23 MOLECULAR SIEVE MATERIAL, ITS SYNTHESIS AND USE

CROSS REFERENCE TO RELATED APPLICATIONS

This application is a divisional of U.S. Ser. No. 14/235,419, filed Mar. 12, 2014, which is a 371 National Stage Application of International Application No. PCT/US2012/047910 filed Jul. 24, 2012, which claims the benefit of and priority to U.S. patent application Ser. No. 61/514,939 filed Aug. 4, 2011 and EP Application No. 11181734.2 filed Sep. 19, 2011, the disclosures of which are incorporated herein by reference in their entireties.

FIELD

This invention relates to a novel molecular sieve material, designated as EMM-23, its synthesis, its use as an adsorbent, and a catalyst for hydrocarbon conversion reactions.

BACKGROUND

Molecular sieve materials, both natural and synthetic, have been demonstrated in the past to be useful as adsorbents and to have catalytic properties for various types of hydrocarbon conversion reactions. Certain molecular sieves, zeolites, AlPOs, mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table Group 13 element oxide (e.g., $AlO_4$). The tetrahedra are cross-linked by the sharing of oxygen atoms with the electrovalence of the tetrahedra containing the Group 13 element (e.g., aluminum) being balanced by the inclusion in the crystal of a cation, for example a proton, an alkali metal or an alkaline earth metal cation. This can be expressed wherein the ratio of the Group 13 element (e.g., aluminum) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

Many zeolites are synthesized in the presence of an organic directing agent, such as an organic nitrogen compound. For example, ZSM-5 may be synthesized in the presence of tetrapropylammonium cations and zeolite MCM-22 may be synthesized in the presence of hexamethyleneimine. It is also known to synthesize zeolites and related molecular sieves in the presence of diquaternary directing agents. For example, U.S. Pat. No. 5,192,521 discloses the synthesis of ZSM-12 in the presence of bis(methylpyrrolidinium)-diquat-n cations, where n=4, 5 or 6.

According to the present invention, a new zeolite structure, designated EMM-23 and having a unique X-ray diffraction pattern, has now been synthesized using bis(N-propylpyrrolidinium)-diquat-n cations, where n is 5 or 6, as a structure directing agent.

SUMMARY

In one aspect, the invention resides in a molecular sieve material having, in its as-calcined form, an X-ray diffraction pattern including the following peaks in Table 1:

TABLE 1

| d-spacing (Å) | Relative Intensity [100 × I/I(o)] |
|---|---|
| 17.5-16.3 | 60-100 |
| 10.6-10.1 | 5-50 |
| 9.99-9.56 | 20-70 |
| 6.23-6.06 | 1-10 |
| 5.84-5.69 | 1-10 |
| 5.54-5.40 | 1-10 |
| 4.29-4.21 | 1-10 |
| 3.932-3.864 | 1-10 |
| 3.766-3.704 | 5-40 |
| 3.735-3.674 | 1-10 |
| 3.657-3.598 | 1-10 |
| 3.595-3.539 | 1-20 |

Conveniently, the molecular sieve material has a composition comprising the molar relationship:

$$X_2O_3:(n)YO_2,$$

wherein n is at least about 10, X is a trivalent element, such as one or more of B, Al, Fe, and Ga, especially Al, and Y is a tetravalent element, such as one or more of Si, Ge, Sn, Ti, and Zr, especially Si.

In another aspect, the invention resides in a molecular sieve material having, in its as-synthesized form, an X-ray diffraction pattern including the following peaks in Table 2:

TABLE 2

| d-spacing (Å) | Relative Intensity [100 × I/I(o)] |
|---|---|
| 17.6-16.3 | 60-100 |
| 11.0-10.5 | 5-40 |
| 10.04-9.60 | 20-70 |

TABLE 2-continued

| d-spacing (Å) | Relative Intensity [100 × I/I(o)] |
|---|---|
| 4.51-4.42 | 1-20 |
| 4.32-4.24 | 1-20 |
| 4.11-4.04 | 1-20 |
| 3.958-3.889 | 5-40 |
| 3.805-3.742 | 20-70 |
| 3.766-3.705 | 5-40 |
| 3.635-3.577 | 1-20 |
| 3.498-3.445 | 1-20 |
| 3.299-3.252 | 1-20 |

Conveniently, the molecular sieve material has a composition comprising the molar relationship:

kF:mQ:X$_2$O$_3$:(n)YO$_2$, wherein 0≤k≤0.2, 0<m≤0.2, n is at least about 10, F is a source of fluoride ion, such as one or more of F, HF, NH$_4$F, and NH$_4$HF$_2$, Q is an organic structure directing agent, X is a trivalent element, such as one or more of B, Al, Fe, and Ga, especially Al and Y is a tetravalent element, such as one or more of Si, Ge, Sn, Ti, and Zr, especially Si.

Conveniently, Q comprises 1,5-bis(N-propylpyrrolidinium)pentane dications and/or 1,6-bis(N-propylpyrrolidinium)hexane dications.

In a further aspect, the invention resides in a process for producing the molecular sieve material described herein, the process comprising the steps of:

(i) preparing a synthesis mixture capable of forming said material, said mixture comprising water, a source of hydroxyl ions, a source of an oxide of a tetravalent element Y, optionally a source of a trivalent element X, optionally a source of fluoride ions (F), and a directing agent (Q) comprising 1,5-bis(N-propylpyrrolidinium)pentane dications and/or 1,6-bis(N-propylpyrrolidinium)hexane dications, and said mixture having a composition, in terms of mole ratios, within the following ranges:

YO$_2$/X$_2$O$_3$ at least 10;
H$_2$O/YO$_2$ about 0.5 to about 30;
OH$^-$/YO$_2$ about 0.1 to about 1.0;
F/YO$_2$ about 0.0 to about 0.25; and
Q/YO$_2$ about 0.05 to about 0.5;

(ii) heating said mixture under crystallization conditions including a temperature of from about 100° C. to about 200° C. and a time from about 1 to about 14 days until crystals of said material are formed; and

(iii) recovering said crystalline material from step (ii).

In one embodiment, said mixture has a composition, in terms of mole ratios, within the following ranges:

YO$_2$/X$_2$O$_3$ at least 100;
H$_2$O/YO$_2$ about 2 to about 10;
OH$^-$/YO$_2$ about 0.2 to about 0.5;
F/YO$_2$ about 0.0; and
Q/YO$_2$ about 0.1 to about 0.25.

In yet a further aspect, the invention resides in a process for converting a feedstock comprising an organic compound to a conversion product which comprises the step of contacting said feedstock with a catalyst at organic compound conversion conditions, said catalyst comprising an active form of the molecular sieve material described herein.

In still yet a further aspect, the invention resides in an organic nitrogen compound comprising a dication having one of the following structures:

BRIEF DESCRIPTION OF THE DRAWINGS

FIGS. 1 (a) and (b) show the X-ray diffraction patterns of the as-synthesized and calcined zeolites, respectively, of Example 4.

FIGS. 2 (a) to (d) are scanning electron micrograph (SEM) images of the product of Example 4 at different magnifications.

FIGS. 3 (a) and (b) are adsorption uptake curves showing, respectively, the adsorption of 2,2-dimethylbutane and 2,3-dimethylbutane at 120° C. by the calcined product of Example 5.

DETAILED DESCRIPTION OF THE EMBODIMENTS

Described herein is a novel molecular sieve material, which is designated EMM-23, its synthesis in the presence of a structure directing agent comprising one or more novel diquaternary ammonium compounds and its use as an adsorbent and a catalyst for organic conversion reactions.

In particular, the novel molecular sieve structure EMM-23 is characterized by an X-ray diffraction pattern which, in the calcined form of the molecular sieve, includes at least the peaks set out in Table 1 below and which, in the as-synthesized form of the molecular sieve, includes at least the peaks set out in Table 2 below.

TABLE 1

| d-spacing (Å) | Relative Intensity [100 × I/I(o)] |
|---|---|
| 17.5-16.3 | 60-100 |
| 10.6-10.1 | 5-50 |
| 9.99-9.56 | 20-70 |
| 6.23-6.06 | 1-10 |
| 5.84-5.69 | 1-10 |
| 5.54-5.40 | 1-10 |
| 4.29-4.21 | 1-10 |
| 3.932-3.864 | 1-10 |
| 3.766-3.704 | 5-40 |
| 3.735-3.674 | 1-10 |
| 3.595-3.539 | 1-20 |

TABLE 2

| d-spacing (Å) | Relative Intensity [100 × I/I(o)] |
| --- | --- |
| 17.6-16.3 | 60-100 |
| 11.0-10.5 | 5-40 |
| 10.04-9.60 | 20-70 |
| 4.51-4.42 | 1-20 |
| 4.32-4.24 | 1-20 |
| 4.11-4.04 | 1-20 |
| 3.958-3.889 | 5-40 |
| 3.805-3.742 | 20-70 |
| 3.766-3.705 | 5-40 |
| 3.635-3.577 | 1-20 |
| 3.498-3.445 | 1-20 |
| 3.299-3.252 | 1-20 |

The X-ray diffraction data reported herein were collected with a PANalytical X-Pert Pro diffraction system, equipped with a X'Celerator detector, using copper K-alpha radiation. The diffraction data were recorded by step-scanning at 0.017 degrees of two-theta, where theta is the Bragg angle, and a counting time of 21 seconds for each step. The interplanar spacings, d-spacings, were calculated in Angstrom units, and the relative peak area intensities of the lines, I/I(o), is one-hundredth of the intensity of the strongest line, above background, were determined with the MDI Jade peak profile fitting algorithm. The intensities are uncorrected for Lorentz and polarization effects. It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

In its calcined form, molecular sieve EMM-23 has a chemical composition comprising the molar relationship:

$X_2O_3:(n)YO_2,$ wherein n is at least about 10, typically greater than about 20, X is a trivalent element, such as one or more of B, Al, Fe, and Ga, especially Al, and Y is a tetravalent element, such as one or more of Si, Ge, Sn, Ti, and Zr, especially Si. It will be appreciated from the permitted values for n that EMM-23 can be synthesized in totally siliceous form in which the trivalent element X is absent or essentially absent.

In its as-synthesized and anhydrous form, molecular sieve EMM-23 has a chemical composition comprising the molar relationship:

$kF:mQ:X_2O_3:(n)YO_2,$ wherein $0 \leq k \leq 0.2$, $0 < m \leq 0.2$, n is at least about 10, typically greater than about 20, F is a source of fluoride, Q is an organic structure directing agent, X is a trivalent element, such as one or more of B, Al, Fe, and Ga, especially Al and Y is a tetravalent element, such as one or more of Si, Ge, Sn, Ti, and Zr, especially Si.

Conveniently, Q comprises 1,5-bis(N-propylpyrrolidinium)pentane dications and/or 1,6-bis(N-propylpyrrolidinium)hexane dications.

The Q and F components, which are associated with the as-synthesized material as a result of their presence during crystallization, are easily removed by conventional post-crystallization methods.

The molecular sieve EMM-23 is thermally stable and in the calcined form exhibits a high surface area and significant hydrocarbon sorption capacity.

EMM-23 can be prepared from a synthesis mixture comprising sources of water, hydroxyl ions, an oxide of a tetravalent element Y, optionally a trivalent element X, optionally a source of fluoride (F) ions, and the structure directing agent (Q) described above, the mixture having a composition, in terms of mole ratios of oxides, within the following ranges:

| Reactants | Useful | Preferred |
| --- | --- | --- |
| $YO_2/X_2O_3$ | at least 10 | at least 100 |
| $H_2O/YO_2$ | 0.5-30 | 2-10 |
| $OH^-/YO_2$ | 0.1-1.0 | 0.2-0.5 |
| $F/YO_2$ | 0-0.25 | 0 |
| $Q/YO_2$ | 0.05-0.5 | 0.1-0.25 |

Suitable sources of the tetravalent element Y depend on the element Y selected; but in the preferred embodiments, in which Y is silicon and/or germanium, include colloidal suspensions of silica, precipitated silica, fumed silica, alkali metal silicates, tetraalkyl orthosilicates and germanium oxide. If present, the trivalent element X is normally aluminum and suitable sources of aluminum include hydrated alumina, aluminum hydroxide, alkali metal aluminates, aluminum alkoxides, and water-soluble aluminum salts, such as aluminum nitrate. If present, suitable sources of fluoride ions include one or more of F, HF, $NH_4F$, and $NH_4HF_2$.

Suitable sources of Q are the hydroxides and/or salts of the relevant diquaternary ammonium compounds. Although the compounds themselves are believed to be novel, they can readily be synthesized by reaction of N-propylpyrrolidine with 1,5-dibromopentane or 1,6-dibromohexane.

The reagents are typically mixed together by a mechanical process such as stirring or high shear blending to assure suitable homogenization of the synthesis mixture. Depending on the nature of the reagents it may be necessary to reduce the amount of water in the mixture before crystallization to obtain the preferred $H_2O/YO_2$ molar ratio. Suitable methods for reducing the water content are evaporation under a static or flowing atmosphere such as ambient air, dry nitrogen, dry air, or by spray drying or freeze drying.

Crystallization of EMM-23 can be carried out at either static or stirred conditions in a suitable reactor vessel, such as for example, polypropylene jars or teflon lined or stainless steel autoclaves, at a temperature of about 100° C. to about 200° C. for a time sufficient for crystallization to occur at the temperature used, e.g., from about 1 day to about 14 days. Thereafter, the crystals are separated from the liquid and recovered.

To the extent desired and depending on the $X_2O_3/YO_2$ molar ratio of the material, any cations in the as-synthesized EMM-23 can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63(5), 27 (1985).

The molecular sieve described herein may be subjected to treatment to remove part or all of the organic directing agent Q used in its synthesis. This is conveniently effected by thermal treatment in which the as-synthesized material is heated at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally-treated product, especially in its metal, hydrogen and ammonium forms, is particularly useful in the catalysis of certain organic, e.g., hydrocarbon, conversion reactions.

The present molecular sieve may be intimately combined with a hydrogenating component, such as molybdenum, tungsten, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The present molecular sieve, when employed either as an adsorbent or as a catalyst should be dehydrated, at least partially. This can be done by heating to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the EMM-23 in a vacuum, but a longer time is required to obtain a sufficient amount of dehydration.

The present molecular sieve can be used as an adsorbent or, particularly in its aluminosilicate form, as a catalyst to catalyze a wide variety of organic compound conversion processes including many of present commercial/industrial importance. Examples of chemical conversion processes which are effectively catalyzed by the crystalline material of this invention, by itself or in combination with one or more other catalytically active substances including other crystalline catalysts, include those requiring a catalyst with acid activity. Examples of organic conversion processes which may be catalyzed by EMM-23 include cracking, hydrocracking, disproportionation, alkylation, oligomerization, and isomerization.

As in the case of many catalysts, it may be desirable to incorporate EMM-23 with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring, or in the form of gelatinous precipitates or gels, including mixtures of silica and metal oxides. Use of a material in conjunction with EMM-23, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with EMM-23 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with EMM-23 also include inorganic oxides, such as silica, zirconia, titania, magnesia, beryllia, alumina, and mixtures thereof.

In addition to the foregoing materials, EMM-23 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of EMM-23 and inorganic oxide matrix may vary widely, with the EMM-23 content ranging from about 1 to about 90 percent by weight, and more usually, particularly when the composite is prepared in the form of beads, in the range of about 2 to about 80 weight percent of the composite.

The invention will now be more particularly described with reference to the following non-limiting Examples and the accompanying drawings.

EXAMPLE 1

A synthesis gel with molar ratios of $H_2O/SiO_2=4$, $Si/Al=50$, and $OH^-/SiO_2=0.5$ was prepared according to the following procedure.

Alumina trihydrate, 0.016 g, was thoroughly mixed with 4.17 g of an aqueous hydroxide solution of 1,5-bis(N-propylpyrrolidinium)pentane ($[OH^{-9}=1.20$ mmol/g) within a tared Teflon liner. Tetramethylorthosilicate (TMOS), 1.54 g, was then added to the mixture. The open liner was then placed in a vented hood in order to allow the methanol and water to evaporate. After 3 days, extra water was added to bring the $H_2O/SiO_2$ molar ratio to 4 (as determined by the total mass of the suspension). The liner was then capped and sealed within an 23 mL steel Parr autoclave. The autoclave was placed on a spit within a convection oven at 150° C. The autoclave was tumbled at 50 rpm over the course of 10 days inside the heated oven. The autoclave was then removed and allowed to cool to room temperature. The solids were then recovered by filtration and washed thoroughly with deionized water (>250 mL) and then acetone (about 20 mL). The solids were allowed to dry in an oven at 100° C. for 2 hours. The resulting product was analyzed by powder XRD and shown to be EMM-23 with minor amount of zeolite beta.

EXAMPLE 2

A synthesis gel with molar ratios of $H_2O/(SiO_2+GeO_2)=4$, $Si/Ge=7.3$, and $OH^-/SiO_2=0.5$ was prepared according to the following procedure.

Germanium oxide, 0.13 g, was thoroughly mixed with 4.17 g of an aqueous hydroxide solution of 1,5-bis(N-propylpyrrolidinium)pentane ([OH$^{-9}$ =1.20 mmol/g) within a tared Teflon liner. TMOS, 1.36 g, was then added to the mixture. The open liner was then placed in a vented hood in order to allow the methanol and water to evaporate. After 3 days, extra water was added to bring the H$_2$O/(SiO$_2$+GeO$_2$) molar ratio to 4 (as determined by the total mass of the suspension). The liner was then capped and sealed within an 23 mL steel Parr autoclave. The autoclave was placed on a spit within a convection oven at 150° C. The autoclave was tumbled at 50 rpm over the course of 10 days inside the heated oven. The product was worked up according to the procedure in Example 1. Powder XRD showed the product to be a mixture of EMM-23 and ITQ-17.

EXAMPLE 3

A synthesis gel with molar ratios of H$_2$O/SiO$_2$=5 and OH$^-$/SiO$_2$=0.5 was prepared according to the following procedure.

An aqueous hydroxide solution of 1,5-bis(N-propylpyrrolidinium)pentane, 4.17 g, ([OH]=1.20 mmol/g) were mixed with 1.54 g TMOS within a tared Teflon liner. Seeds, 0.02 g of the product from Example 1, were added to the gel. Two small steel balls (about 4 mm in diameter) were next added to the synthesis gel. The open liner was then placed in a vented hood in order to allow the methanol and water to evaporate. After 3 days, extra water was added to bring the H$_2$O/SiO$_2$ ratio to 5 (as determined by the total mass of the suspension). The liner was then capped and sealed within an 23 mL steel Parr autoclave. The autoclave was placed on a spit within a convection oven at 150° C. The autoclave was tumbled at 50 rpm over the course of 6 days inside the heated oven. The product was worked up according to the procedure in Example 1. Powder XRD showed the product to be a mixture of EMM-23 and amorphous material.

EXAMPLE 4

A synthesis gel with molar ratios of H$_2$O/SiO$_2$=5, Si/Al=75, and OH$^-$/SiO$_2$=0.5 was prepared according to the following example.

Alumina trihydrate, 0.013 g, was thoroughly mixed with 4.71 g of an aqueous hydroxide solution of 1,5-bis(N-propylpyrrolidinium)pentane ([OH$^{-9}$ =1.20 mmol/g) within a tared Teflon liner. TMOS, 1.74 g, was then added to the mixture. Seeds, 0.02 g of the product from Example 1, were added to the gel. Two small steel balls (about 4 mm in diameter) were next added to the synthesis gel. The open liner was then placed in a vented hood in order to allow the methanol and water to evaporate. After 2 days, extra water was added to bring the H$_2$O/SiO$_2$ molar ratio to 5 (as determined by the total mass of the suspension). The liner was then capped and sealed within an 23 mL steel Parr autoclave. The autoclave was placed on a spit within a convection oven at 150° C. The autoclave was tumbled at 50 rpm over the course of 6 days inside the heated oven. The product was worked up according to the procedure in Example 1. The lines of the X-ray diffraction pattern of the as-synthesized product are given in Table 3. The A % is the intensity of the peak relative to the most intense peak in the pattern.

TABLE 3

| 2-Theta (degrees) | d(Å) | A % |
|---|---|---|
| 5.22 | 16.903 | 100 |
| 8.25 | 10.706 | 19.7 |
| 9.00 | 9.818 | 38 |
| 12.77 | 6.926 | 3.5 |
| 13.73 | 6.446 | 4.4 |
| 15.13 | 5.853 | 2.4 |
| 15.58 | 5.682 | 1.4 |
| 16.46 | 5.382 | 1.9 |
| 17.97 | 4.933 | 1.7 |
| 18.74 | 4.731 | 2.6 |
| 19.86 | 4.467 | 6.6 |
| 20.14 | 4.405 | 4.3 |
| 20.75 | 4.277 | 7.7 |
| 21.80 | 4.074 | 6.9 |
| 22.07 | 4.024 | 2.4 |
| 22.65 | 3.923 | 11 |
| 23.56 | 3.773 | 31.7 |
| 23.80 | 3.736 | 12 |
| 24.42 | 3.642 | 5.3 |
| 24.67 | 3.606 | 7 |
| 25.64 | 3.471 | 6.7 |
| 26.02 | 3.421 | 3.3 |
| 26.88 | 3.315 | 6 |
| 27.05 | 3.294 | 5.4 |
| 27.20 | 3.275 | 9.3 |
| 27.54 | 3.236 | 1.4 |
| 27.71 | 3.217 | 1.4 |
| 28.29 | 3.152 | 0.8 |
| 29.06 | 3.070 | 3.7 |
| 29.75 | 3.001 | 3.6 |
| 29.99 | 2.977 | 1.1 |
| 30.71 | 2.909 | 1.5 |
| 31.43 | 2.844 | 0.5 |
| 31.82 | 2.810 | 2.3 |
| 32.49 | 2.754 | 4 |
| 33.75 | 2.654 | 1.5 |
| 34.33 | 2.610 | 0.6 |
| 35.04 | 2.559 | 2.1 |
| 35.90 | 2.499 | 0.3 |
| 36.70 | 2.447 | 1 |
| 36.95 | 2.431 | 0.5 |
| 37.35 | 2.406 | 1.4 |
| 37.84 | 2.376 | 0.6 |
| 38.09 | 2.361 | 0.5 |
| 38.35 | 2.345 | 0.4 |
| 38.58 | 2.332 | 0.6 |
| 39.04 | 2.305 | 0.5 |
| 39.60 | 2.274 | 0.7 |
| 40.07 | 2.248 | 0.7 |
| 40.38 | 2.232 | 0.4 |
| 41.18 | 2.190 | 0.4 |
| 41.79 | 2.160 | 1.5 |
| 42.77 | 2.113 | 0.5 |
| 43.36 | 2.085 | 0.7 |
| 43.83 | 2.064 | 0.9 |
| 44.24 | 2.046 | 0.7 |
| 44.61 | 2.030 | 2.1 |
| 45.26 | 2.002 | 1.3 |
| 45.79 | 1.980 | 1.6 |
| 46.13 | 1.966 | 1.6 |
| 46.64 | 1.946 | 0.4 |
| 47.11 | 1.928 | 0.5 |
| 47.84 | 1.900 | 2.4 |
| 48.46 | 1.877 | 0.7 |
| 49.06 | 1.855 | 1.1 |
| 49.72 | 1.832 | 1.1 |

Figure 1:
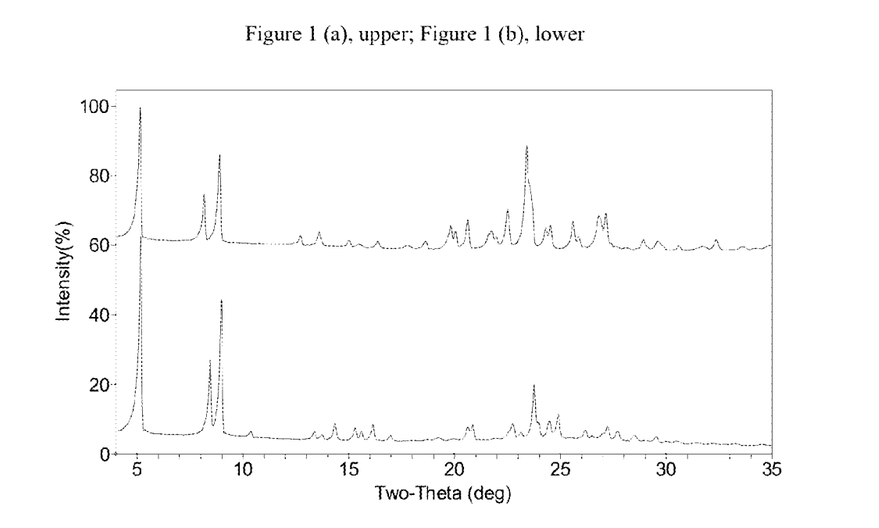

A portion of the resultant product was calcined according to the following procedure. The zeolite was heated inside a muffle furnace from ambient temperature to 400° C. at 4° C./min under a nitrogen atmosphere, then heated to 550° C. at 4° C./min in air, and maintained at 550° C. in air for 2 hours. FIGS. 1 (a) and (b) show the powder XRD patterns of the as-synthesized and calcined zeolites, respectively, and indicate the material to be pure EMM-23. The lines of the X-ray diffraction pattern of the calcined product is given in Table 4.

TABLE 4

| 2-Theta (degrees) | d(Å) | A % |
|---|---|---|
| 5.23 | 16.880 | 100 |
| 8.51 | 10.382 | 21.9 |
| 9.04 | 9.773 | 43.6 |
| 13.43 | 6.589 | 2.2 |
| 13.79 | 6.418 | 1.3 |
| 14.41 | 6.144 | 4.1 |
| 15.35 | 5.769 | 2.6 |
| 15.65 | 5.660 | 1.7 |
| 16.20 | 5.469 | 3.8 |
| 17.02 | 5.205 | 1.5 |
| 18.83 | 4.708 | 0.4 |
| 19.29 | 4.598 | 1 |
| 20.02 | 4.431 | 0.5 |
| 20.67 | 4.293 | 2.5 |
| 20.91 | 4.246 | 3 |
| 21.97 | 4.043 | 0.3 |
| 22.58 | 3.935 | 0.9 |
| 22.80 | 3.898 | 3.5 |
| 23.19 | 3.833 | 1.3 |
| 23.80 | 3.735 | 10.6 |
| 24.01 | 3.704 | 3.2 |
| 24.52 | 3.627 | 4.1 |
| 24.94 | 3.567 | 5.6 |
| 26.22 | 3.397 | 1.5 |
| 26.54 | 3.356 | 0.5 |
| 27.01 | 3.298 | 1 |
| 27.27 | 3.268 | 2.5 |
| 27.74 | 3.213 | 1.9 |
| 28.55 | 3.124 | 1.4 |
| 29.02 | 3.075 | 0.4 |
| 29.56 | 3.020 | 1.1 |
| 30.03 | 2.973 | 0.3 |
| 30.56 | 2.923 | 0.6 |
| 31.53 | 2.835 | 0.5 |
| 33.31 | 2.688 | 0.4 |
| 34.61 | 2.589 | 0.3 |

Figure 2:
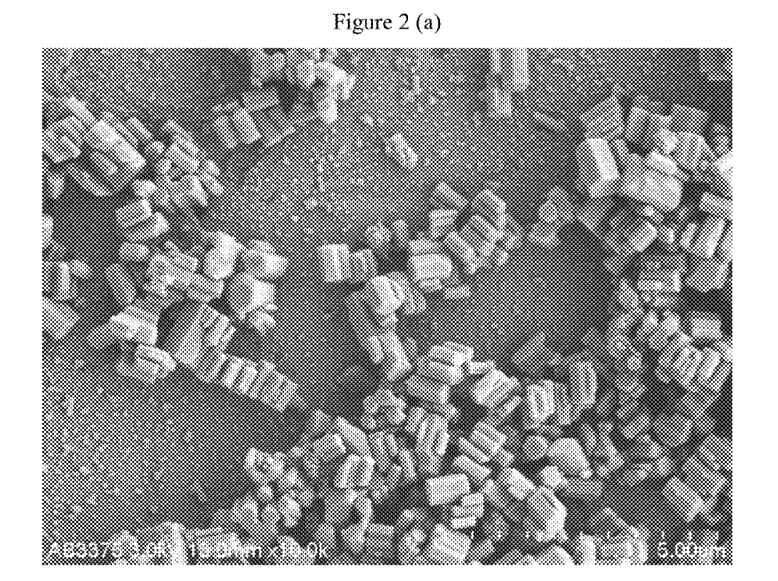

Scanning electron micrograph (SEM) images of the product of Example 4 at different magnifications are shown in FIGS. 2 (a) to (d).

EXAMPLE 5

Example 3 was repeated except that 0.02 g of seeds from Example 4 were used instead of seeds from Example 1. The product was worked up after 4 days of heating at 150° C. Powder XRD showed the product to be pure EMM-23.

EXAMPLE 6

Example 5 was repeated except the heating period was extended to 7 days. Powder XRD showed the product to be pure EMM-23.

EXAMPLE 7

Example 4 was repeated with Si/Al=50 and with 0.02 g seeds from Example 4 being used instead of seeds from Example 1. The product was worked up after 6 days of heating at 150° C. Powder XRD showed the product to be pure EMM-23.

EXAMPLE 8

An as-made sample from Example 4 was placed within a tube furnace supplied with dry air flow through an ozone generator. The sample was first heated to 150° C. in the presence of flowing air (3500 mL/min), and then the ozone generator was then switched on to give 1-1.2% ozone to the tube furnace. After heating the sample at 150° C. for a total of 5 hours in the presence of ozone, the ozone generator was switched off and the reactor was allowed to cool to ambient temperatures. Powder XRD indicates that the sample remains crystalline after this treatment (Table 3 shows the characteristic peaks) but that the peak positions and intensities are different from those of the sample calcined to 550° C. Thermogravimetric analysis and mass spectrometry (TGA/MS) indicate that the sample contains no carbonaceous material after the treatment with ozone. A portion of the sample was dried under vacuum at 300° C. and flame sealed in a 1 mm quartz capillary. Table 5 gives the XRD pattern taken using synchrotron radiation at λ=0.8668 and a 2-theta step size=0.005 degrees.

TABLE 5

| 2-Theta (degrees) | d(Å) | A % |
|---|---|---|
| 2.92 | 17.001 | 100 |
| 4.65 | 10.675 | 37.1 |
| 5.06 | 9.815 | 47.4 |
| 5.85 | 8.498 | 1.5 |
| 7.25 | 6.858 | 2.4 |
| 7.74 | 6.425 | 3.2 |
| 7.82 | 6.359 | 5 |
| 8.54 | 5.818 | 4.3 |
| 8.78 | 5.665 | 4.5 |
| 8.85 | 5.620 | 4.9 |
| 9.32 | 5.336 | 1.7 |
| 10.55 | 4.714 | 0.8 |
| 10.61 | 4.689 | 1.2 |
| 11.15 | 4.460 | 0.2 |
| 11.27 | 4.415 | 1.7 |
| 11.39 | 4.368 | 4.1 |
| 11.71 | 4.250 | 4 |
| 12.26 | 4.060 | 0.8 |
| 12.36 | 4.026 | 2.9 |
| 12.47 | 3.991 | 1.7 |
| 12.76 | 3.900 | 2.9 |
| 12.81 | 3.885 | 2.1 |
| 13.27 | 3.751 | 18.6 |
| 13.36 | 3.725 | 8.7 |
| 13.42 | 3.710 | 6.2 |
| 13.78 | 3.612 | 3.5 |
| 13.90 | 3.581 | 5.7 |
| 13.99 | 3.558 | 0.9 |
| 14.52 | 3.429 | 3.6 |
| 14.65 | 3.400 | 2.8 |
| 15.17 | 3.283 | 4 |
| 15.22 | 3.272 | 4 |
| 15.39 | 3.238 | 7.6 |
| 15.50 | 3.213 | 0.9 |
| 15.66 | 3.181 | 1.3 |
| 15.93 | 3.129 | 0.6 |
| 16.36 | 3.047 | 3.6 |
| 16.48 | 3.025 | 0.3 |
| 16.72 | 2.981 | 1.4 |
| 16.80 | 2.967 | 2.1 |
| 16.88 | 2.953 | 0.8 |
| 16.99 | 2.934 | 0.3 |
| 17.30 | 2.881 | 1.7 |
| 17.85 | 2.794 | 0.8 |
| 17.98 | 2.774 | 0.8 |
| 18.28 | 2.728 | 2.5 |
| 18.33 | 2.721 | 0.2 |
| 18.42 | 2.708 | 0.2 |
| 18.98 | 2.629 | 1.1 |
| 19.25 | 2.592 | 0.5 |
| 19.64 | 2.542 | 0.5 |
| 19.78 | 2.523 | 0.9 |
| 20.21 | 2.470 | 0.3 |
| 20.56 | 2.429 | 0.8 |

TABLE 5-continued

| 2-Theta (degrees) | d(Å) | A % |
|---|---|---|
| 20.73 | 2.409 | 0.9 |
| 20.93 | 2.386 | 0.6 |
| 21.06 | 2.372 | 0.3 |
| 21.18 | 2.358 | 0.4 |
| 21.35 | 2.340 | 0.7 |
| 21.67 | 2.306 | 0.2 |
| 21.84 | 2.288 | 0.3 |
| 22.16 | 2.255 | 0.2 |
| 22.43 | 2.229 | 0.4 |
| 22.65 | 2.207 | 0.3 |
| 23.35 | 2.142 | 0.9 |
| 23.87 | 2.095 | 0.2 |
| 23.98 | 2.086 | 0.2 |
| 24.19 | 2.069 | 0.3 |
| 24.34 | 2.056 | 0.2 |
| 24.48 | 2.044 | 0.4 |
| 24.65 | 2.030 | 0.4 |
| 24.78 | 2.020 | 0.2 |
| 25.26 | 1.982 | 0.5 |
| 25.41 | 1.971 | 0.8 |
| 25.50 | 1.964 | 0.5 |
| 25.57 | 1.959 | 0.4 |
| 25.67 | 1.951 | 0.8 |
| 25.75 | 1.945 | 0.6 |
| 25.96 | 1.930 | 0.5 |
| 26.19 | 1.913 | 0.8 |
| 26.47 | 1.893 | 0.4 |
| 26.61 | 1.883 | 0.6 |
| 26.74 | 1.875 | 1.2 |
| 27.06 | 1.853 | 0.6 |
| 27.21 | 1.843 | 0.5 |
| 27.28 | 1.838 | 0.3 |
| 27.60 | 1.817 | 0.3 |
| 27.73 | 1.809 | 0.4 |
| 28.14 | 1.783 | 0.6 |
| 28.39 | 1.767 | 0.5 |
| 28.70 | 1.749 | 0.2 |
| 28.83 | 1.741 | 0.4 |
| 29.21 | 1.719 | 0.8 |
| 29.58 | 1.698 | 0.5 |
| 29.73 | 1.690 | 0.5 |
| 30.01 | 1.674 | 1 |
| 30.28 | 1.659 | 0.5 |

EXAMPLES 9 to 19

A series of small scale syntheses were run within the 1.5 cc wells of a parallel synthesis reactor. Each of the syntheses used a new stainless steel liner with a steel ball. In each Example, TMOS was the source of silica. Where present, germanium oxide was the source of germanium, and aluminum nitrate was the source of aluminum. In Examples 9 to 15, the structure directing agent was 1,5-bis(N-propylpyaolidinium)pentane dihydroxide, whereas in Examples 16 to 19 the structure directing agent was 1,6-bis(N-propylpyrrolidinium)hexane dihydroxide. The composition of each of the synthesis mixtures (in molar ratios) is summarized in Table 7 below.

TABLE 7

| Example | H$_2$O/(Si + Ge) | Si/Ge | Si/Al | HF/(Si + Ge) | SDA(OH)$_2$/ (Si + Ge) |
|---|---|---|---|---|---|
| Syntheses with 1,5-bis(N-propylpyrrolidinium)pentane dihydroxide | | | | | |
| 9 | 4 | 4 | — | 0 | 0.25 |
| 10 | 4 | 7.3 | — | 0 | 0.25 |
| 11 | 4 | — | — | 0.125 | 0.25 |
| 12 | 4 | — | 100 | 0 | 0.25 |
| 13 | 4 | — | 100 | 0.125 | 0.25 |

TABLE 7-continued

| Example | H$_2$O/(Si + Ge) | Si/Ge | Si/Al | HF/(Si + Ge) | SDA(OH)$_2$/ (Si + Ge) |
|---|---|---|---|---|---|
| 14 | 4 | — | — | 0 | 0.25 |
| 15 | 10 | — | 100 | 0.125 | 0.25 |
| Syntheses with 1,6-bis(N-propylpyrrolidinium)hexane dihydroxide | | | | | |
| 16 | 4 | 4 | — | 0 | 0.25 |
| 17 | 4 | 7.3 | — | 0 | 0.25 |
| 18 | 4 | — | 100 | 0 | 0.25 |
| 19 | 4 | — | 100 | 0.125 | 0.25 |

After addition of the reactants, the reaction mixtures were freeze-dried to remove most of the water and methanol and then water was added to adjust the H$_2$O/SiO$_2$ molar ratio to the designated level. The reactor was rotated in rotisserie oven at 150° C. for 10 days. The products were worked up by 2 iterations of centrifugation and washings with deionized water and in each case the product was pure EMM-23.

EXAMPLE 20

The calcined product of Example 5 was tested for its capacity to adsorb n-hexane at 90° C., 2,2-dimethylbutane and 2,3-dimethylbutane at 120° C. and the results are summarized below:

| | |
|---|---|
| n-hexane | 120 mg/g |
| 2,2-dimethylbutane | 73 mg/g |
| 2,3-dimethylbutane | 75 mg/g |

Figure 3:
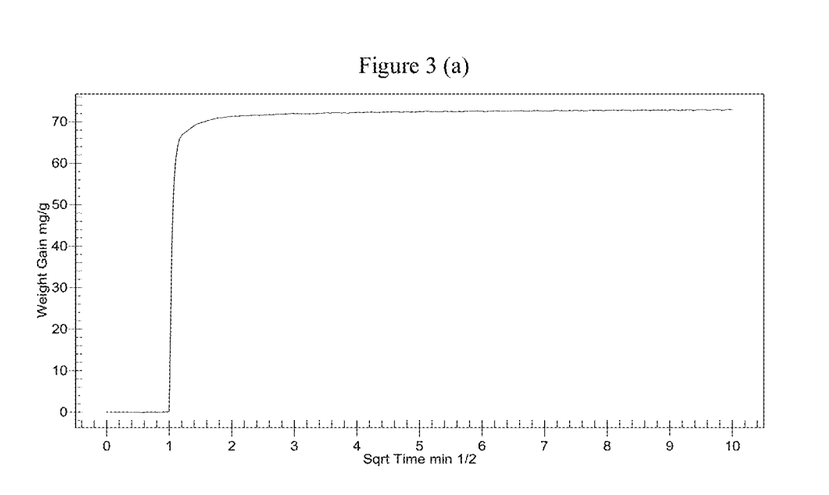

Adsorption uptake curves showing the adsorption of 2,2-dimethylbutane and 2,3-dimethylbutane at 120° C. by the product of Example 5 are shown in FIGS. 3 (a) and (b), respectively.

The adsorption data suggest that EMM-23 is a molecular sieve including pores defined by 12-membered ring of tetrahedrally coordinated atoms.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. An organic nitrogen compound comprising a dication having the following structure:

wherein said organic nitrogen compound is 1,5-bis(N-propylpyrrolidinium)pentane dication.

2. An organic nitrogen compound comprising a dication having the following structure:

wherein said organic nitrogen compound is 1,6-bis(N-propylpyrrolidinium)pentane dication.

* * * * *